United States Patent [19]

Goldstein

[11] 4,223,552

[45] Sep. 23, 1980

[54] APPARATUS AND METHOD FOR SENSING A SUBSTANCE ON A LIQUID SURFACE

[75] Inventor: Sanders Goldstein, Cambridge, Mass.

[73] Assignee: Emhart Industries, Inc., Indianapolis, Ind.

[21] Appl. No.: 22,622

[22] Filed: Mar. 21, 1979

[51] Int. Cl.³ ...................... G01N 25/18; G01N 33/18
[52] U.S. Cl. ................................................. 73/61.1 R
[58] Field of Search .............................. 73/61.1 R, 53

[56] References Cited

U.S. PATENT DOCUMENTS

| | | | |
|---|---|---|---|
| 3,576,472 | 4/1971 | Marshall | 73/15 R X |
| 3,712,116 | 1/1973 | Andre | 73/53 |
| 3,720,797 | 3/1973 | Gunn et al. | 73/61.1 R X |
| 4,058,802 | 11/1977 | Meyers | 73/61.1 R X |
| 4,116,045 | 9/1978 | Potter | 73/61.1 R |
| 4,131,773 | 12/1978 | Maham et al. | 200/61.05 |

FOREIGN PATENT DOCUMENTS

| | | | |
|---|---|---|---|
| 2319427 | 4/1973 | Fed. Rep. of Germany | 73/61.1 R |
| 569904 | 8/1977 | U.S.S.R. | 73/61.1 R |
| 615404 | 7/1978 | U.S.S.R. | 73/61.1 R |

*Primary Examiner*—Gerald Goldberg
*Assistant Examiner*—Joseph W. Roskos
*Attorney, Agent, or Firm*—Robert F. Meyer; David W. Gomes

[57] ABSTRACT

A sensing element is embedded in an absorbant material having a substantial affinity for the substance to be sensed and a relatively low affinity for the liquid. A measurable quantity of the substance is concentrated in proximity to the sensing element and accurately positioning the sensing element in the material the thickness of the substance on the liquid surface is determinable.

11 Claims, 2 Drawing Figures

APPARATUS AND METHOD FOR SENSING A SUBSTANCE ON A LIQUID SURFACE

The present invention relates to an apparatus for sensing a substance on a liquid surface and particularly for sensing thin films and for measuring the thickness of the substance. An application of the invention is in detecting a substance such as oil and other hydrocarbon spills on a water surface.

Generally speaking, the apparatus of the present invention includes one or more sensing elements such as diodes, zener diodes, thermistors, or transistors embedded in an absorbent material having a substantial affinity for the substance and a relatively low affinity for the liquid. The absorbent material concentrates the substance in proximity to the sensing element or elements so that a very thin film of the substance may be sensed. By accurately positioning the element or elements in the material, the thickness of the substance may also be measured. Importantly, the sensing element is isolated from the liquid and is therefore insensitive to the temperature, flow, and turbulence of the liquid.

In a co-pending application assigned to P. R. Mallory & Co. Inc. entitled "Apparatus And Method For Detecting The Presence Of A Substance On A Liquid Surface" Ser. No. 019,147, a system is disclosed for detecting the presence or absence of a substance on a liquid surface. Other systems are also disclosed in U.S. Pat. Nos. 3,576,472; 3,712,116; and 4,116,045 which are intended to accomplish the same or similar results i.e. the detection of a substance on a liquid surface. In each of these systems the sensing elements are positioned in direct contact with the liquid. Some of the sensing elements are positioned at the surface and other sensing elements are positioned beneath the surface. Furthermore, in order to operate accurately the sensing element on the surface must be carefully positioned and maintained at the interface of the liquid and the substance.

Accordingly, detection systems such as those disclosed in the exemplary application and patents discussed above have been plagued with the following problems: (1) inability to sense and detect very thin films of a substance; (2) inability to measure the thickness of the substance; (3) the adverse effect on the accuracy of operation due to flow or turbulence of the liquid; (4) the adverse effect on the accuracy of operation due to ambient temperature changes of the liquid; (5) the adverse effect on the accuracy of operation due to contaminates in the liquid other than the substance to be detected; and (6) how to clean the sensing element once it has become coated with the substance being detected. These problems have significantly limited the application of prior detection systems.

One aspect of the present invention is to provide an apparatus for sensing a substance on a liquid surface which senses very thin films of the substance by concentrating measurable quantities of the substance in proximity to a sensing element. Another aspect is the accurate positioning of a plurality of sensing elements within an absorbent material to measure various thicknesses of the substance on the liquid surface. The absorbent material has a substantial affinity for the substance and a relatively low affinity for the liquid. Still another aspect of the present invention is the isolation of the sensing element or elements from the liquid whereby the sensing element is insensitive to the temperature, flow, turbulence, and other contaminants of the liquid and is not dependent upon an exact positioning of the sensing element at the liquid-substance interface for accuracy of operation.

The apparatus of the present invention has no moving parts and is therefore not susceptible to mechanical failure and is disposable so that the problem of how to clean the sensing element once it becomes coated with the substance is eliminated. Furthermore, the apparatus is provided with terminal means allowing for quick and easy replacement of the apparatus.

A method in accordance with the present invention includes the step of isolating a sensing element from the liquid by embedding it in an absorbent material having a substantial affinity for the substance to be sensed and a relatively low affinity for the liquid and concentrating a measurable quanity of the substance in proximity to the sensing element.

Other features and advantages of the present invention will be apparent from the following detailed description of a preferred embodiment thereof, which description should be considered in conjunction with the accompanying drawings in which.

As previously indicated, the sensing of very thin films of a substance on a liquid surface and the sensitivity of sensing elements to temperature, flow, and turbulence of the liquid have heretofore been significant problems associated with the utilization of detection systems such as those disclosed in the application and patents discussed above. The present invention solves not only these problems but also many other problems associated with sensing the presence or the absence of a substance on a liquid surface and in addition provides means for measuring the thickness of the substance.

Figure 1:
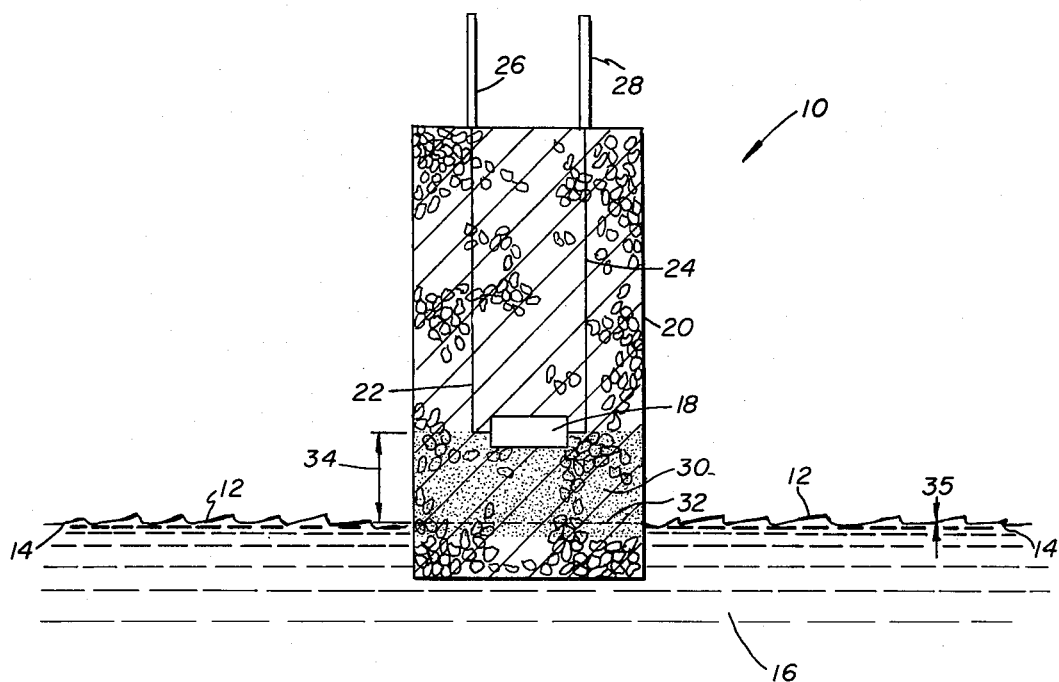
FIG. 1 is a cross-sectional view of an embodiment of the present invention shown in conjunction with a liquid and a substance to be sensed.

Referring to FIG. 1, an apparatus 10 for sensing a substance 12 on the surface 14 of a liquid 16 as constructed in accordance with the present invention includes a sensing element 18 embedded in an absorbent material 20. In the embodiment illustrated the absorbent material 20 is cylindrical in shape however, it will be understood that the material 20 may be any shape without departing from the spirit of the present invention. Sensing element 18 has associated therewith a pair of electrical leads 22 and 24 each at least partially embedded in the material 20 and extending upwardly away from the liquid 16 where they each are electrically and mechanically connected to a pair of terminals 26 and 28 respectively protruding outwardly from the material 20 for quick and easy connection of the sensing element 18 and the apparatus 10 to associated detection circuitry (not shown) and a supporting member (not shown) such as a flotation collar or similar supporting device if required.

For purposes of describing the invention, the liquid 16 is water, although not necessarily free of contaminates such as salts and various minerals, and the substance 12 is oil or other liquid hydrocarbons such as kerosene and gasoline. It will be understood by those skilled in the art that the present invention is adaptable for sensing various other substances in various other liquids without departing from the spirit or essence of the invention described herein.

The sensing element 18 may be any one of a number of sensing elements such as diodes (including zener diodes), thermistors, transistors, filaments, etc, which have heretofore been used for sensing the presence or absence of a substance 12 on a liquid surface 14. Typically, a sensing element 18 have been employed where an electrical characteristic of the sensing element 18 is responsive to the thermal conductivity of the liquid 16, substance 12 or other medium e.g. material 20 in proximity thereto. Each of these monitoring or sensing elements have necessarily had to be accurately positioned and maintained at the interface of the substance 12 and the liquid 16 in order to sense the presence or absence of the substance 12 on the liquid surface 14. Employing these sensing elements has resulted in considerable difficulty in sensing very thin films of the substance 12 e.g. films having a thickness less than the radius of the sensing element 18. Again, for purposes of describing the present invention the sensing element 18 is a diode.

The absorbent material 20 should have a very high affinity for the substance 12 to be sensed and a very low affinity for the liquid 16 within which the apparatus 10 is to be immersed so that over a period of time, with the presence of the substance 12 on the liquid surface 14, the material 20 will have a high concentration of the substance 12 and a very low concentration of the liquid 16. An example of an oleophilic material 20 which is presently used to absorb oil on a water surface and which therefore may be employed in the present invention is "Oil Sorbent" Type 156 manufactured by 3M Company, Saint Paul, Minn. In a manner to be described hereinafter the absorbent material 20 serves as a "wick" which by absorbing the substance 12 concentrates a measurable quantity 30 of the substance 12 in proximity to the sensing element 18. Accordingly, even films of the substance 12 having a thickness of 0.01 inches or less can be sensed. Furthermore, the absorbent material 20 serves to isolate the sensing element from the liquid 16 so that temperature changes, flow, and turbulence of the liquid 16 do not affect the operation of the sensing element 18.

Preferably, the apparatus 10 will have some buoyancy associated therewith so that a reference point 32 in proximity to the liquid surface 14 will substantially follow the liquid surface 14 in response to turbulence. If the absorbent material 20 itself is buoyant in the liquid 16 no supporting member may be necessary. However, in order to preclude bobbing and tipping of the apparatus 10 in turbulent liquids 16 it is desirable that the apparatus 10 be coupled to a flotation device of some sort having the capability of lending stability to the apparatus 10 in turbulent liquids 16. Numerous commercial devices are available to accomplish the desired stability and therefore it is not crucial to the present invention which device is used as long as the apparatus 10 is buoyant and stabilized.

By accurately positioning the sensing element 18 in the absorbent material 20 a predetermined distance 34 from the reference point 32 the thickness 35 of the substance 12 can be measured. Importantly, it should be understood that the distance 34 will be determined by a calibration of distances 34 verses various thicknesses of the substance 12 so that the positioning of the sensing element 18 at a predetermined distance 34 from the reference point 32 is indicative of a known thickness 35 of the substance 12. Furthermore, it should be noted that the distance 34 for a known thickness 35 of the substance 12 will be influenced by various properties of the substance 12 to be sensed e.g. the viscosity of the substance 12. Accordingly, the accurate positioning of the sensing element 18 establishes a preset threshold which when the substance 12 is concentrated in a measurable quantity 30 in proximity to the sensing element 18 provides an indication of the thickness 35 of the substance 12. One means for calibrating the distance 34 utilizes the known rate of absorption or diffusion of various substances by the absorbent material 20. In accordance with this known rate the time required for a substance to be absorbed a distance 34 from a fixed point point 32 is known and therefore a time calibration may be used.

Due to the simple and inexpensive nature of apparatus 10 it is intended that the apparatus 12 will be a disposable unit. Accordingly, the problem of how to clean the sensing element 18 after being coated with the substance 12 is solved by merely replacing the entire apparatus 10. Terminals 26 and 28 are provided to allow easy removal of the old apparatus 10 and connection to the replacement unit.

In operation, as the substance 12 accumulates on the liquid surface 14, the absorbent material 20 begins to absorb measurable quantities 30 of the substance 12. As the substance 12 continues to accumulate, the measurable quantity 30 will eventually contact the sensing element 18 whereby the presence of the substance 12 is sensed and the thickness 35 of the substance 12 is indicated in accordance with previous calibrations of the apparatus 10. The smaller the distance 34, the thinner the film of substance 12 which can be sensed. The thickness 35 of the substance 12 is indicated when the measurable quantity 30 of the substance 12 contacts the sensing element 12 by the fact that the distance 34 has been previously calibrated to represent a known thickness. Furthermore, it should be noted that thin films of the substance 12 may also be sensed by embedding the sensing element 18 in a very small piece of the absorbent material 20 whereby a very small quantity of the substance will quickly saturate the material 20. The smaller the quantity of material the thinner the thickness of oil which may be sensed.

Figure 2:
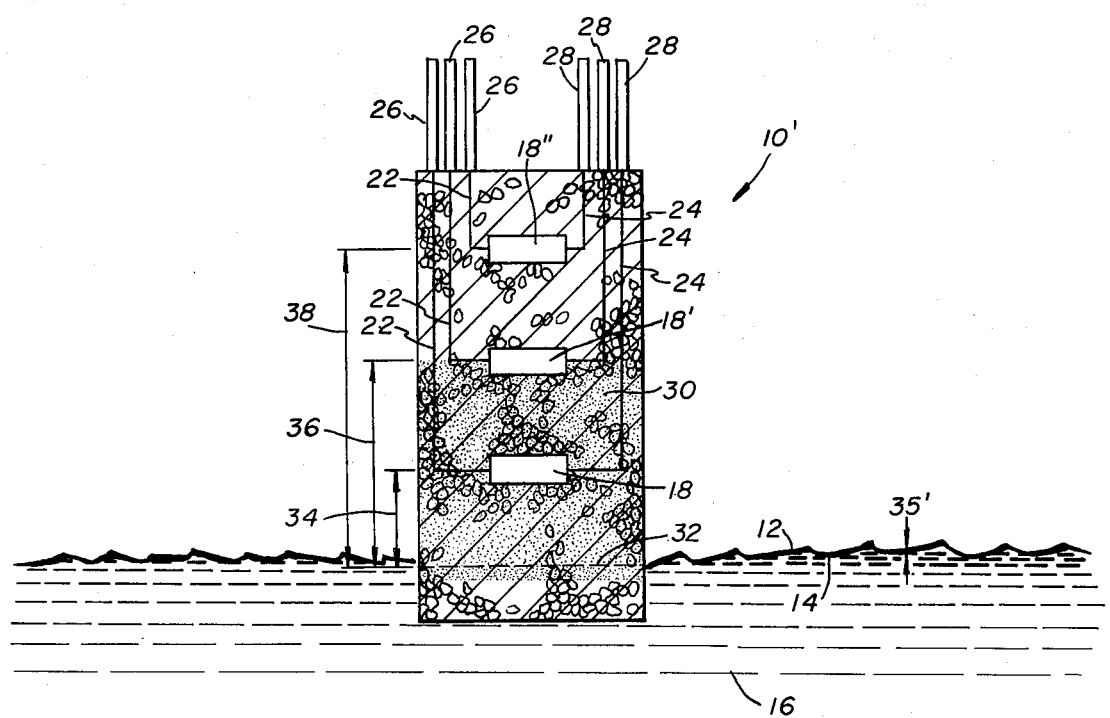
FIG. 2 is a cross-sectional view of an embodiment of the apparatus illustrated in FIG. 1 adapted to measure various thicknesses of the substance on the liquid surface.

In referring to FIG. 2, various elements of the apparatus 10' shown in FIG. 2 which are the same as elements previously described and shown in FIG. 1 have been identified by the same reference numerals and are therefore not described in detail hereafter. In FIG. 2, an apparatus 10' for performing all of the same functions associated with the apparatus 10 shown in FIG. 1 is also capable of measuring a plurality of thicknesses of the substance 12. By embedding a plurality of sensing elements 18, 18' and 18" in the absorbent material 20 and accurately positioning the sensing elements 18, 18' and 18" at predetermined vertical distances 34, 36, and 38 from the reference point 32, various thicknesses 35' of the substance 12 can be measured. Furthermore, the apparatus 10' is capable of sensing an increase in the thickness 35' of substance 12 as a function of time. Each distance 34, 36, and 38 is indicative of a known thickness of the substance 12 and therefore as each sensing element 18, 18' and 18" senses the substance 12; the thickness 35' of the substance 12 is measured.

What is claimed is:

1. An apparatus for sensing a substance on a liquid surface comprising: at least one sensing element embedded in an absorbent material having a substantial affinity for said substance, said sensing element positioned in said material a predetermined distance from a reference point located in proximity to said liquid surface thereby establishing a threshold indicative of a known thickness of said substance, further comprising a plurality of sensing elements embedded in said material, said sensing elements being positioned in said material at various predetermined distances from said reference point thereby establishing a plurality of thresholds for measuring the thickness of said substance on said liquid surface.

2. A method of sensing a substance on a liquid surface comprising the steps of: isolating a sensing element from said liquid with a material; establishing a threshold indicative of a known thickness of said substance by positioning said sensing element in said material a predetermined distance from a reference point in proximity to said liquid surface; concentrating a measurable quantity of said substance in proximity to said sensing element; and measuring the thickness of said substance on said liquid surface by establishing a plurality of thresholds indicative of various known thicknesses of said substance.

3. The method as recited in claim 2 wherein said plurality of thresholds are established by positioning a plurality of sensing elements in said material at various predetermined distances from said reference point.

4. An apparatus for sensing a substance on a liquid surface comprising:
at least one sensing element;
means for locating said sensing element a predetermined distance from said liquid surface; and
a mass of absorbent material for contacting said liquid surface, said sensing element being embedded in said material and said material having a substantial absorption affinity for said substance and a relatively low absorption affinity for said liquid for allowing said substance to be absorbed by said material and thereby rise above said liquid surface to said sensing element and for preventing said liquid from saturating said material up to said sensing element, wherein said predetermined distance and the speed of absorption of said substance from said liquid surface to said sensing element allows a determination of the amount of substance on said liquid surface.

5. The apparatus of claim 4, wherein said means for establishing a predetermined distance includes said mass of absorbent material being boyant in said liquid.

6. The apparatus of claim 4, wherein said predetermined distance is short for allowing the sensing of smaller amounts of said substance.

7. The apparatus of claim 4, wherein said sensing element and said mass of absorbent material are disposable.

8. The apparatus of claim 4, wherein said absorbent material surrounds said sensing element for isolating said element from said liquid and thereby insensitize said element to the flow and temperature of said liquid.

9. The apparatus of claim 4, further comprising a second sensing element embedded in said absorbent material at a second predetermined distance above first said sensing element for allowing a determination of the amount of said substance on said liquid surface in response to the speed of absorption of said substance between first said and said second sensing elements over said second predetermined distance.

10. A method for sensing a substance on a liquid surface comprising the steps of:
locating a sensing element a predetermined distance above said liquid surface by embedding said element within absorbent material and contacting said material with said liquid surface, said absorbent material having a substantial absorption affinity for said substance and a relatively low absorption affinity for said liquid for allowing said substance to saturate said material above said liquid surface up to said sensing element and preventing said liquid from saturating said substance above said liquid surface; and
measuring the amount of time taken by said substance to be absorbed over said predetermined distance as a determination of the amount of said substance on said liquid surface.

11. The method of claim 10, further comprising locating at least one additional sensing element a second predetermined distance above first said sensing element by embedding said second sensing element within said absorbent material, and measuring the time of absorption of said substance between first said and said second elements to enable determination of the amount of substance on said liquid surface.

* * * * *